United States Patent [19]
Desjardins et al.

[11] Patent Number: 5,309,213
[45] Date of Patent: May 3, 1994

[54] OPTICAL DETERMINATION OF AMOUNT OF SOOT IN OIL SAMPLE

[75] Inventors: John B. Desjardins, Watertown; William W. Seifert, Wellesley Hills; Vernon C. Westcott, Lincoln, all of Mass.

[73] Assignee: Analysts, Inc., Torrance, Calif.

[21] Appl. No.: 846,385

[22] Filed: Mar. 5, 1992

[51] Int. Cl.⁵ .................... G01N 21/03; G01N 21/59
[52] U.S. Cl. ........................... 356/70; 356/246; 356/436; 356/440
[58] Field of Search ............... 356/70, 436, 440, 246, 356/409, 413; 250/576

[56] References Cited

U.S. PATENT DOCUMENTS

| | | | |
|---|---|---|---|
| 1,940,772 | 12/1933 | Schoenberg | 356/70 |
| 3,829,217 | 8/1974 | Johnson et al. | 356/70 |
| 4,938,602 | 7/1990 | May et al. | 356/435 |

OTHER PUBLICATIONS

Robertson et al. "Lambert Absorption Coefficients of Water in the Infrared" *Journal of the Optical Society of America* vol. 61, No. 10 (Oct. 1971) pp. 1316–1320.

Tyler et al. "Thin-wedge-shaped cell for highly absorbent liquids" *Applied Optics*, vol. 17, No. 6 (Mar. 15, 1978) pp. 960–963.

Primary Examiner—Richard A. Rosenberger
Attorney, Agent, or Firm—Parmelee, Bollinger & Bramblett

[57] ABSTRACT

Method and apparatus for determining the concentration of optically attenuating materials in fluids, such as soot in diesel engine lubricating oils. An optical cell is employed in the form of a very thin tapered sample volume which is inserted into a light beam. The attenuation of the beam is measured at a plurality of locations along the varying thickness of the sample.

8 Claims, 2 Drawing Sheets

OPTICAL DETERMINATION OF AMOUNT OF SOOT IN OIL SAMPLE

TECHNICAL FIELD

This invention pertains to the field of photometric analysis. More particularly, it pertains to the measurement of opacity such as results from soot particles in diesel engine lubricating oil.

BACKGROUND ART

The most common pollutant of the lubricating oil used in diesel engines is soot. Diesel engine lubricating oils normally contain a dispersant for maintaining the soot particles in suspension. It is important, for economical operation of such an engine, to be able to determine when the dispersant has been substantially used up. In this manner, the lubricating oil can be changed at the most economically advantageous time. Changing the oil substantially prior to the full utilization of the dispersant is wasteful but going beyond such point might cause damage to the engine. Accordingly, it would be helpful to have a simple method of testing the soot content of a small sample of lubricating oil.

It would also be important that any such test be run quickly and that it be accurate and inexpensive. Such a test would be particularly useful, for example, for operators of long haul trucks.

It might appear obvious to make a simple optical determination of soot particles in oil by placing an oil sample in a conventional cell bounded by parallel glass plates and shining a light therethrough to a detector. However, that is not the case. For example, when new or only slightly used diesel oil is examined in such a cell, the oil is frequently too clear to permit an accurate measurement. On the other hand, oil which has been used for some time is often too opaque to determine the soot concentration. As a result, such a cell is usable only to measure a limited range of concentrations. This problem may be overcome by using several different cells or by carefully diluting the oil samples.

Accordingly, it is a primary object of the present invention to provide an improved optical cell for determining soot concentration in lubricating oil other objects are to provide such a cell which is simple in construction, which is simple to use, which is usable through a wide range of soot concentrations, which does not require calibration against ano cell or instrument, and which produces accurate and reproducible results. The manner in which these objects are achieved will be apparent from the following description and appended claims.

DISCLOSURE OF INVENTION

The cell of this invention comprises a wedge which retains the sample between a pair of glass plates. The cell is advanced through a light beam between a light source and a detector. Attenuation of the beam increases as the sample thickness in the wedge increases. This provides a readout giving the desired information.

BEST MODE FOR CARRYING OUT THE INVENTION

This invention operates upon the principle of Beers' law which is, itself, an extension of Lambert's law. According to Lambert's law, radiation which traverses a thin layer of matter is reduced in intensity in proportion to the thickness of the layer. Beers' law states that, in the case of two solutions which are similar except that the first contains twice the concentration of an absorbing or scattering substance of the second, the attenuation of light (including the effects of absorption and scattering) due to a given thickness of the first solution is equal to that of twice the thickness of the second.

As light passes through an absorbing fluid, the fractional change in intensity per unit of fluid thickness is constant. Assuming a fluid that is uniform throughout the light path, the fractional reduction of light intensity with unit thickness is the same along the whole path. Thus, the attenuation of light can be expressed as a certain fraction per unit thickness. Because this relationship is logarithmic, and because it is desirable to express the readings with as few digits as possible, attenuation is expressed as decibels per micrometer. A decibel is ten times the base ten logarithm of the intensity ratio.

Figure 1:
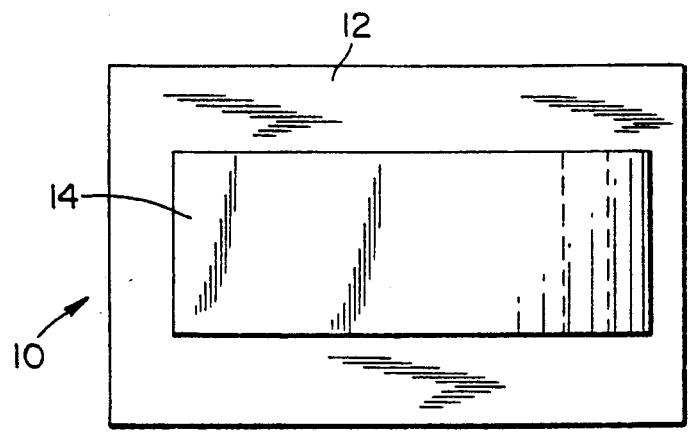
FIG. 1 is a plan view of an optical cell in accordance with the invention.
Figure 2:
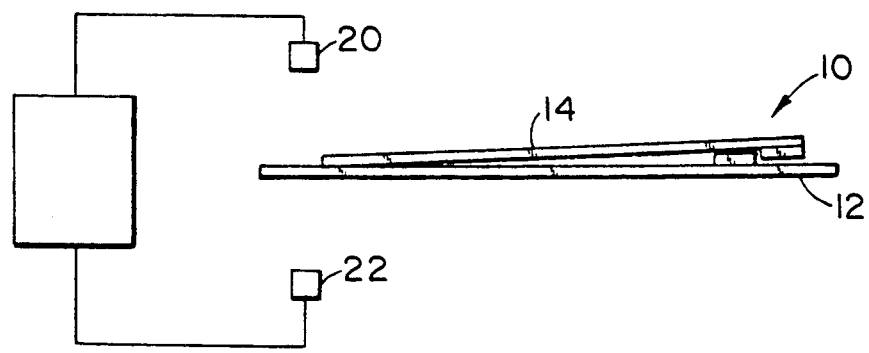
FIG. 2 is an elevational view of the cell of FIG. 1 showing diagramatically the light source and detector.
Figure 3:
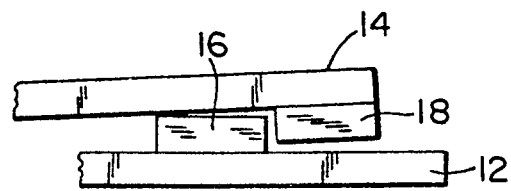
FIG. 3 is an enlarged detail as viewed from 3—3 of FIG. 1.

The cell 10 of this invention is illustrated in FIGS. 1-3. It is formed from a pair of polished glass plates. The lower or base plate 12 is longer and wider than the upper or cover plate 14. Mounted upon the base plate 12 is a thin strip of glass forming a pillar 16. The length of pillar 16 is preferably at least equal to the width of the cover plate 14. Mounted to one end of cover plate 14 on its underside is a thin glass plate forming a catch 18.

The dimensions of the members forming cell 10 are not critical. However, in one embodiment the width of the cover plate 14 is 25 millimeters. The distance from the left end of cover plate 14 (as viewed in FIG. 1) to the edge of the pillar 16 is 55 millimeters. The thickness of pillar 16 is 1 millimeter and it is engaged by the catch 18 as illustrated in FIG. 3. The catch 18 serves to prevent the cover plate 14 from sliding off the pillar 16. Accordingly, its thickness is immaterial so long as it does not contact the base plate 12. In addition, the catch 18, by acting to limit the active length and position of the cover plate 14 relative to the base plate 12 and pillar 16 reproducibly defines the wedge angle of the cell. This angle may be approximately 1".

Figure 4:
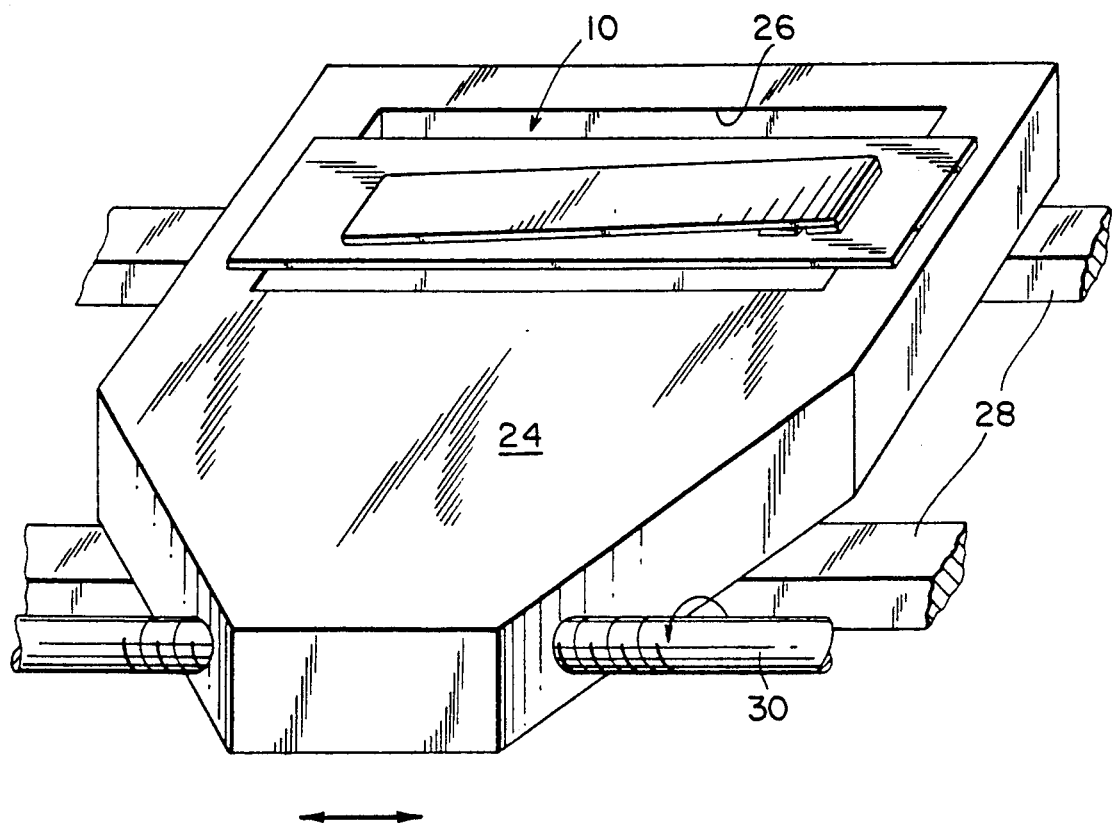
FIG. 4 is a perspective view of a portion of an instrument utilizing the cell of the invention.

As will be noted from FIG. 2, the cell 10 is positioned between a light source 20, which may be a fiber-optic source, and a detector 22, which may be a silicon light-detecting cell. The cell is prepared for use by depositing a small sample (about one ml) of the oil to be tested upon the base plate 12. The cover plate 14 is then lowered onto the sample until it is supported at one end by the base plate 12 and at the other end by the pillar 16. The surface tension of the oil is sufficient to hold the assembly together. Initially, the cell is completely outside the light path and it is advanced into the light path beginning with the thin edge of the wedge-shaped cell. One method of accomplishing this is illustrated in FIG. 4 wherein the cell 10 is shown resting upon a cradle 24. The cell 10 sits over an opening 26, permitting light from the source 20 to reach the detector 22 (not shown).

The cradle 24 slides along a pair of rails 28 by means of a rotating precision screw 30.

A computer may be employed to initiate rotation of the screw 30, which drives the cell 10 into the light path. As the thin end of the cell enters the light path, the intensity of the light signal on the detector 22 is continuously measured and the resulting signal is digitized. When a thick enough section of the sample cell intercepts the beam so that significant attenuation is observed, the computer automatically begins to save the successive digitized values. The digital values of photo detector current are stored and later converted into decibels of attenuation. The stored values, along with the position of the cradle 24 for each point, make it possible to generate data points of attenuation versus film thickness. These data are employed to determine a straight line using a least squares regression to thereby determine decibels attenuation per micrometer for the sample. After the reading is obtained, the cradle 24 is backed out of the light path where it is accessible to a technician to load a new sample.

It has been determined that the readings obtained by the method of this invention are proportional to the concentration of soot in oil. As long as the observations follow both Lambert's and Beers' Laws, a number will be generated which is proportional to the mass concentration of soot in the oil. These numbers are convertible into mass concentrations simply by multiplying them by a constant.

Among the advantages of this cell is the fact that it is not necessary to determine a zero point. Also, a traditional cell having a fixed light path normally requires a complementary measurement made with an identical cell filled with clear oil. Furthermore, cells with parallel windows are subject to reflections which affect the readings. With the tapered, variable path length, cell of this invention, it is only the change in light intensity versus cell position that contributes to the measurement.

The dynamic range of this cell is extremely large. This is because the range is determined by the product of the dynamic range of the light measuring apparatus multiplied by the range of thicknesses obtainable from the cell.

The accuracy of the output may be expressed as a percentage of the reading. Most instruments must be rated for accuracy in terms of percentage of full scale, which is much less desirable. Since only the change of light attenuation with film thickness is involved, it makes no difference whether the fluid contains only a small amount of soot or a high concentration. High accuracy is obtained in either case.

The technique of this invention ignores micelles of dark gelatinous material floating in the oil. These are small compared to the area of the light beam and have little effect on the reading. Another reason for the immunity to absorbing bodies such as dark micelles, large particles, small air bubbles, etc. is that the contribution of such artifacts is minimized by the least squares regression analysis.

The successive readings are fundamentally independent because each data point is taken through a different light path. This results in a "homogenizing" or "averaging" effect. Accordingly, any factor that causes errors in only a few readings is significantly reduced or eliminated. An air bubble in the sample is an example of such a factor.

It is believed that the many advantages of this invention will now be apparent to those skilled in the art. It will also be apparent that a number of variations and modifications may be made therein without departing from its spirit and scope. For example, it will be obvious that the invention is usable, not only for determination of soot in oil, but for measurement of any opacity creating substance in fluid. Accordingly, the foregoing description is to be construed as illustrative only, rather than limiting. This invention is limited only by the scope of the following claims.

We claim:

1. A method for analyzing an oil sample for soot suspending therein which comprises:
   providing an optically transparent tapered cell;
   placing a sample of said oil within said cell;
   providing a light source on one side of said cell;
   providing a light detector on the opposite side of said cell;
   passing visible light along a path from said source, through said cell and oil, and onto said detector;
   moving said cell and light path relative to one another whereby the length of the light path through said sample contained within the cell is progressively altered from a first to a second value as a result of the different thicknesses of the sample;
   generating a signal proportional to the intensity of the light impinging on said detector; and
   utilizing the measured values of said impinging light measured through said first and second light paths to determine the attenuation per length of said path as a representation of the soot concentration in the sample.

2. The method of measuring the amount of soot in oil comprising the steps of:
   configuring a sample of said oil in the shape of a tapered wedge providing progressively increasing thickness dimensions at different positions along the wedge;
   transmitting visible light through said sample at said different wedge positions;
   developing relative movement between said sample and the path of said transmitted light to provide that the length of the light path is progressively altered at said different wedge positions as a result of the wedge shape of the sample; and
   making measurements of the light transmitted through said sample at predetermined intervals during said relative movement to determine the change in attenuation corresponding to the change in path length and thereby to determine the average mass concentration of said soot substantially free of the effects of artifacts therein.

3. The method of measuring the amount of soot in oil comprising the steps of:
   configuring a sample of said oil in such a shape as to provide progressively different thicknesses at predetermined different locations;
   transmitting visible light through said sample at said different locations in a sequential series of light transmissions such that the length of the light path through said sample is progressively altered as a result of said progressively different thicknesses of the sample;
   making measurements of the light transmitted through said progressively different lengths of light path through said sample at said different locations; and using the measurements of light through progressively different light path lengths to determine a straight-line relationship of attenuation per path length representing the concentration of soot in the sample.

4. The method of measuring the amount of soot in oil comprising the steps of:

configuring a sample of said oil in such a shape as to provide progressively different thicknesses at predetermined different locations;

transmitting visible radiant energy through said sample at said different locations in a sequential series of transmissions such that the length of the radiant energy path through said sample is progressively altered as a result of said progressively different thicknesses of the sample;

making measurements of the radiant energy transmitted through said progressively different lengths of light path through said sample at said different locations; and using the measurements of radiant energy through said progressively different path lengths to determine an at least approximately straight-line relationship representing attenuation per path length corresponding to the concentration of soot in the sample.

5. A method for analyzing an oil sample for soot therein which comprises:

providing an optically transparent tapered cell;

placing a sample of said oil within said cell;

providing a visible light source on one side of said cell;

providing a light detector on the opposite side of said cell;

passing light along a path from said source, through said cell and oil, and onto said detector;

moving said cell and light path relative to one another whereby the portion of the light path length traversing the oil contained within the cell varies between a first and a second value;

generating a signal proportional to the intensity of the light impinging on said detector during said relative movement;

storing successive digital values of the received light intensity corresponding to different path lengths; and determining from said stored values the accentuation per unit path length to indicate the concentration of soot in said oil sample.

6. The method of claim 5, wherein said stored values are employed to determine a straight line representing a reading of attenuation in decibels per unit length.

7. The method of claim 5, wherein the reading is converted into mass concentration by multiplying it by a constant.

8. The method of measuring the amount of soot in oil comprising the steps of:

configuring a sample of said oil in such a shape as to provide progressively different thicknesses at predetermined different locations;

transmitting visible light through said sample at said different locations in a sequential series of transmissions such that the length of the visible light path through said sample is progressively altered as a result of said progressively different thicknesses of the sample making measurements of the intensity of visible light transmitted through said progressively different lengths of light path through said sample at said different locations;

storing successive digital values of the measured light intensity corresponding to said different path lengths; and determining from said stored values the attenuation per unit path length as an indication of the concentration of soot in said oil sample.

* * * * *